United States Patent [19]
Miller

[11] 4,417,087
[45] Nov. 22, 1983

[54] FLUIDIZED OLIGOMERIZATION

[75] Inventor: Stephen J. Miller, San Francisco, Calif.

[73] Assignee: Chevron Research Company, San Francisco, Calif.

[21] Appl. No.: 373,479

[22] Filed: Apr. 30, 1982

[51] Int. Cl.$^3$ .............................................. C07C 2/02
[52] U.S. Cl. ................................... 585/530; 585/517; 585/533
[58] Field of Search ....................... 585/517, 530, 533

[56] References Cited

U.S. PATENT DOCUMENTS

| | | | |
|---|---|---|---|
| 2,678,904 | 5/1954 | Kearby et al. | 208/71 |
| 4,032,432 | 6/1977 | Owen et al. | 208/70 |
| 4,066,531 | 1/1978 | Owen et al. | 208/120 |
| 4,090,949 | 5/1978 | Owen et al. | 208/78 |
| 4,238,318 | 12/1980 | Kouwenhoven et al. | 585/418 |

Primary Examiner—Curtis R. Davis
Attorney, Agent, or Firm—D. A. Newell; S. R. La Paglia; W. L. Stumpf

[57] ABSTRACT

A fluidized oligomerization process is disclosed.

15 Claims, 2 Drawing Figures

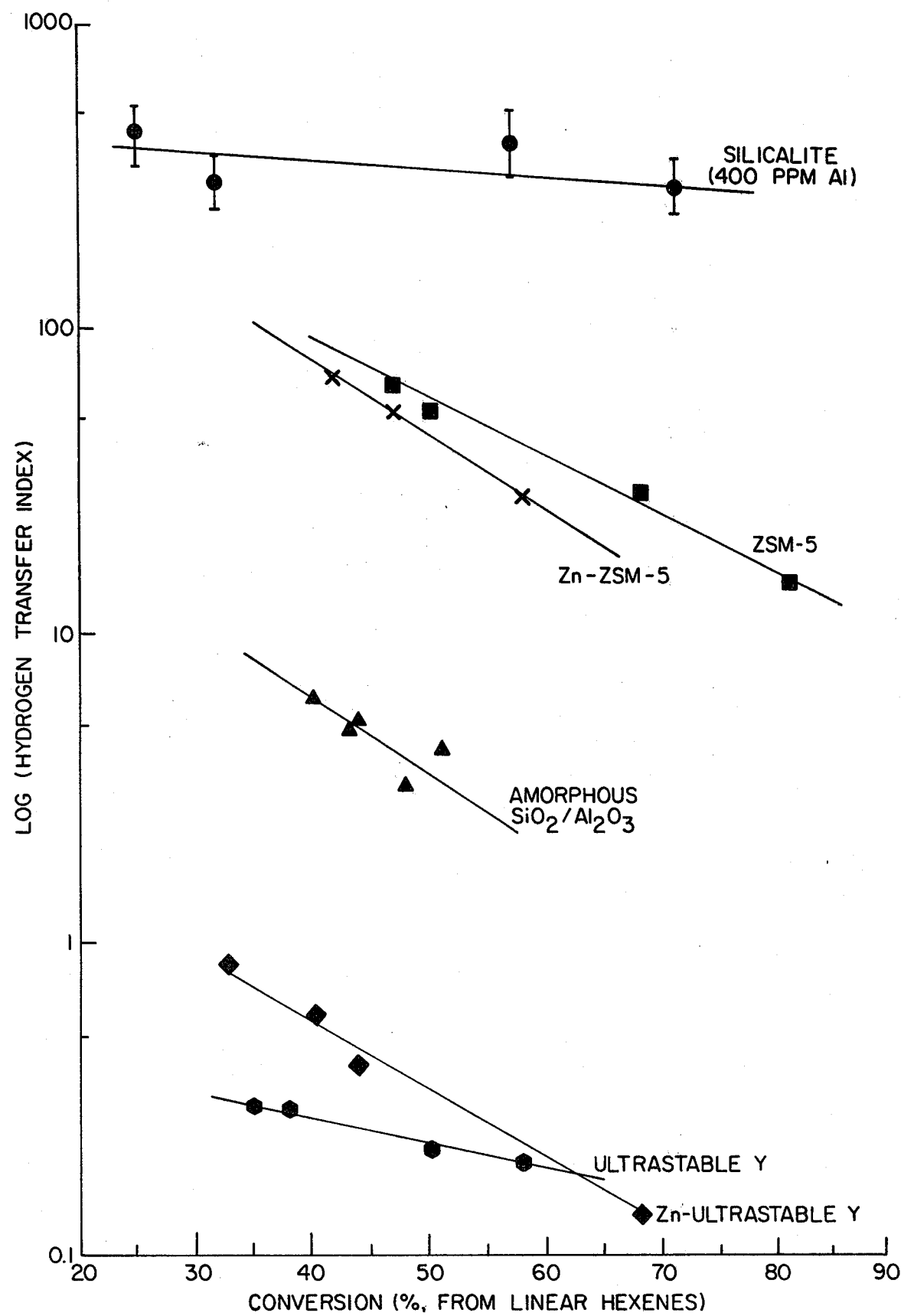
FIG._1.

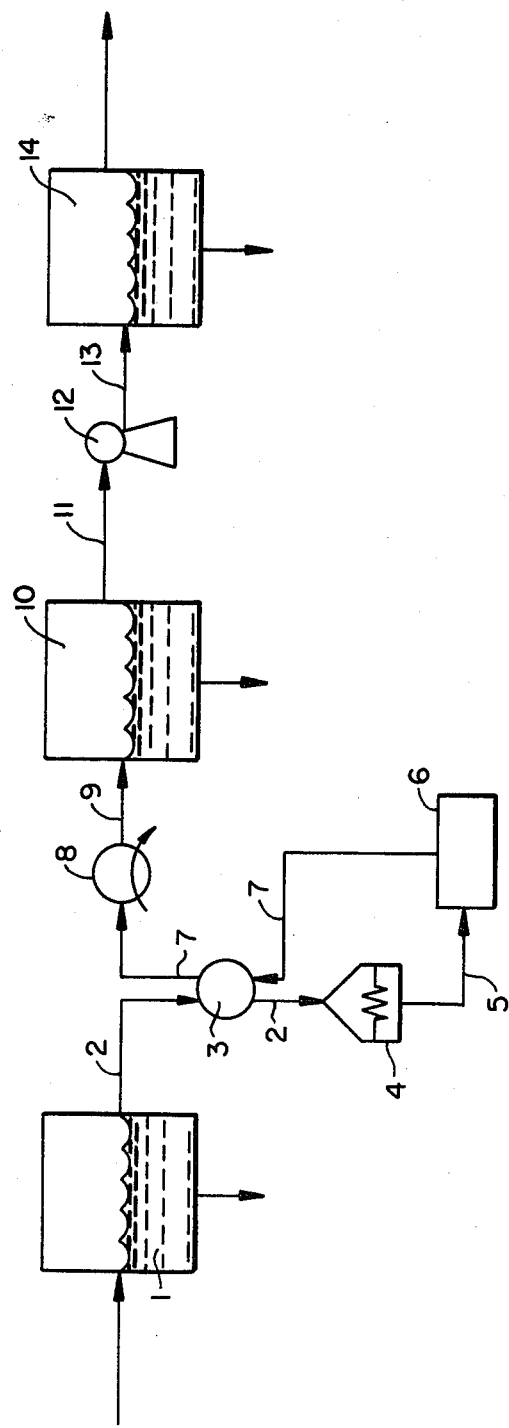
FIG._2.

FLUIDIZED OLIGOMERIZATION

TECHNICAL BACKGROUND

One of the continuing problems in the refinery when using catalytic cracking processes is handling the very large amounts of gas produced. Catalytic cracking, and especially fluid catalytic cracking (FCC), is widely used in petroleum refineries in the United States. Refiners in the United States have more capacity for catalytic cracking than for any other single process except distillation. Those refiners have the capacity to catalytically crack over 6,100,000 barrels of oil per day (*Oil and Gas Journal*, Mar. 24, 1980). Since catalytic cracking is a nonhydrogenative process, it can be appreciated that huge amounts of olefinic gases are produced. Whenever the severity of a catalytic cracker is increased or the feed throughput is increased, even more olefinic gases are produced.

Recovering these enormous amounts of gas for further reaction requires large capital outlays for compressors and gas handling equipment. The alternative is to burn the olefinic gases as fuel for other parts of the refinery or as waste. Unfortunately, because the quantities of gas are huge and capital costs high, these gases are too often burned instead of recovered and reacted.

It can be appreciated that there is a highly intensive search for efficient, economical processes which would allow these reactive olefinic gases to be used further as chemicals, rather than to be wasted, but which do not require massive capital expenditures. This search for more efficient methods of using olefinic gases has continued for some time. U.S. Pat. No. 2,678,904, Kearby et al., May 18, 1954, for example, discloses polymerizing the olefins present in catalytic cracker effluent using a fluidized reaction bed containing an amorphous silica-alumina cracking catalyst. Other methods, using zeolites, have been proposed for processing heavier materials. U.S. Pat. No. 4,006,531, Owen et al., Jan. 3, 1978, discloses preparing the aromatic benzene, toluene, and the xylenes, from heavy reformates using zeolites and fluidized beds. U.S. Pat. No. 4,090,949, Owen et al., May 23, 1978, discloses upgrading poor quality olefinic gasolines by converting them in the presence of carbon/hydrogen contributing fragments using zeolites and fluidized beds. A recent disclosure relates to a combination process for catalytically cracking gas oils and upgrading the $C_6^-$ products using the same dual component zeolite catalyst in both steps. U.S. Pat. No. 4,032,432, Owen, June 28, 1977.

I have discovered that certain silicaceous crystalline molecular sieves can be used in a fluidized reaction zone to produce substantial amounts of olefin oligomers from the normally gaseous olefins produced by catalytic cracking. By oligomerizing all or part of the olefins, the volume of gas that needs to be handled is greatly decreased, plus, substantial amounts of more useful higher molecular weight olefin compounds are produced. Further, the fluidized oligomerization process can operate at the same pressure as the FCC reactor; the need for compressors is greatly lessened. This highly significant advantage occurs even if only part of the gas stream is fed to the oligomerization reactor. Importantly, because oligomerization is highly exothermic, the heat generated by the oligomerization reaction can be used to heat the feed to the oligomerization zone; the process is energy efficient by saving fuel as well as by saving the electricity which would be required for the compressors.

Additionally, the catalysts used are highly stable and the reaction conditions are mild so that the catalyst charge to the oligomerization zone can have a very long service life merely by periodically, or continuously, stripping the charge with hot gas. The necessity of burning to remove coke is greatly lowered.

All of these advantages are achieved by fluidized oligomerization using essentially aluminum-free intermediate pore size silicaceous crystalline molecular sieve catalysts.

TECHNICAL DISCLOSURE

My discoveries are embodied in a process comprising introducing a feed comprising gaseous olefins into an oligomerization reaction zone, under oligomerization reaction conditions, wherein said reaction zone contains a fluidizable oligomerization catalyst which comprises an essentially aluminum-free intermediate pore size silicaceous crystalline molecular sieve, such that said feed fluidizes said catalyst and at least 30% of said feed olefins are converted to higher boiling olefins.

My discoveries are also embodied in a process comprising:

(a) recovering the normally gaseous portion of the effluent of a catalytic cracking zone; and (b) introducing a feed comprising at least part of said effluent into an oligomerization reaction zone, under oligomerization reaction conditions, wherein said reaction zone contains a fluidizable oligomerization catalyst which comprises an essentially aluminum-free intermediate pore size silicaceous crystalline molecular sieve such that said feed fluidizes said catalyst and at least 30% of said feed olefins are converted to higher boiling olefins.

The feed olefins can be prepared from any source by standard methods. The feed need only contain olefins which are gaseous under the reaction conditions, as opposed to liquid olefins, so the catalyst bed can be fluidized. The most preferred olefins are those which are normally gaseous. Sources of such lower olefins can include FCC offgas, syngas (by use of CO reduction catalysts), low pressure, nonhydrogenative zeolite dewaxing, alkanols (by using high silica zeolites), dewaxing with crystalline silica polymorphs, and thermal cracking offgas. The olefins can contain up to 6 or 7 carbon atoms but are preferably propene, $C_4$ olefins, and their mixtures. The preferred feed sources are FCC offgas, nonhydrogenative zeolite dewaxing offgas, and offgas from dewaxing with crystalline silica polymorphs.

The preferred olefins, if process streams are not used, are straight chain, or n-olefins, and the preferred n-olefins are 1-olefins.

By "essentially aluminum-free intermediate pore size silicaceous crystalline molecular sieve," as used herein, is meant materials which are essentially free of aluminum. These crystalline materials can include crystalline silica polymorphs, e.g., silicalite as disclosed in U.S. Pat. No. 4,061,724, Grose et al., Dec. 6, 1977, incorporated by reference; chromia silicates, e.g., CZM; and ferrosilicates, such as are disclosed in U.S. Pat. No. 4,238,318, Kouwenhoeven et al., Dec. 9, 1980, incorporated by reference.

All of these materials have the ability of sorting molecules based on the size of the shape, or both of the molecules. The larger pore size materials will admit larger molecules than the smaller pore size materials. Intermediate pore size siliceous crystalline molecular sieves have the unique characteristics of being able to differentiate between large molecules and molecules containing quaternary carbon atoms on the one hand, and smaller molecules on the other. Thus, the intermediate pore size materials have surprising selectivities by reason of their effective pore apertures, as well as highly desirable and surprising activity and stability when compared to larger pore size crystalline molecular sieves.

By "intermediate pore size," as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size, or kinetic pore size, of molecular sieves can be measured using standard adsorption techniques, and hydrocarbonaceous compounds of known minimum kinetic diameters. See Breck, *Zeolite Molecular Sieves,* 1974 (especially Chapter 8) and Anderson et al., J. Catalysis 58, 114 (1979), both of which are incorporated by reference.

Intermediate pore size molecular sieves in the H-form will typically admit molecules having kinetic diameters of 5.0 and 6.5 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), 2,2-dimethylbutane (6.2), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 3.5 to about 6.2 Angstroms.

In performing adsorption measurements to determine pore size, standard techniques are used. It is convenient to consider a particular molecule as excluded if it does not reach at least 95% of its equilibrium adsorption value on the molecular sieve in less than about 10 minutes (p/po=0.5; 25° C.).

By "essentially aluminum-free," as used herein, is meant that the product siliceous crystalline molecular sieve has a silica:alumina mole ratio of greater than 200:1, preferably greater than 500:1, and more preferably greater than 1000:1. The term "essentially aluminum-free" is used because it is difficult to prepare reaction mixtures completely free of aluminum for synthesizing these molecular sieves. Especially when commercial silica sources are used, aluminum is almost always present to a greater or lesser degree. The hydrothermal reaction mixtures from which the essentially aluminum-free crystalline siliceous molecular sieves are prepared can also be referred to as being substantially aluminum free. By this usage is meant that no aluminum is intentionally added to the reaction mixture, e.g., as an alumina or aluminate reagent, and that to the extent aluminum is present, it occurs only as a contaminant in the reagents. The silica source should contain less than about 2500 ppm aluminum, preferably less than about 1500 ppm aluminum, and most preferably less than about 1250 ppm aluminum.

Intermediate pore size siliceous crystalline molecular sieves include silicalite, disclosed in U.S. Pat. No. 4,061,724; and the "RE 29,948 organosilicates" as disclosed in U.S. Pat. No. Re. 29,948, Dwyer et al., Mar. 27, 1979. Intermediate pore size silicas, ferrosilicates and galliosilicates are disclosed in U.S. Pat. No. 4,238,318, Kouwenhoven et al., Dec. 9, 1980. Intermediate pore size chromia silicates, CZM, are disclosed in Ser. No. 160,618, Miller, filed June 28, 1980. All of these are incorporated by reference.

The most preferred molecular sieves are silicalite, U.S. Pat. No. Re. 29,948 organosilicates, and CZM. The most highly preferred molecular sieve catalyst comprises the attrition-resistant particles disclosed in my copending Ser. No. 375,439, filed May 6, 1982, and incorporated by reference.

The siliceous crystalline molecular sieve catalysts can be made surprisingly more active and stable for oligomerization by including Group IIB metals, zinc or cadmium. A primary characteristic of these substituents is that they are weak bases, and are not easily reduced. These metals can be incorporated into the catalysts using standard impregnation, ion exchange, etc., techniques. Other metals such as calcium and the rare earths may be included in the catalyst. If hydrogen is not added to the feed, Group VIII metals (e.g., nickel, cobalt, palladium, and platinum) as well as other metals (e.g., vanadium, titanium, manganese and rhenium) may be included in the catalyst. Mixtures of the metals may also be present. Strongly basic metals such as the alkali metals are unsatisfactory as they poison substantially all of the polymerization sites on the molecular sieve. For this reason, the alkali metal content of the molecular sieve is less than 1%, preferably less than 0.1%, and most preferably less than 0.01%. The most preferred substituent for use is zinc.

The molecular sieves can be composited with inorganic matrix materials, or they can be used with an organic binder. Standard methods for incorporating molecular sieves into FCC catalysts and for preparing fluidizable catalysts can be used to prepare the fluidizable oligomerization catalysts. It is preferred to incorporate the molecular sieve into an inorganic matrix since the molecular sieves, because of their large internal pore volumes, tend to be fragile, and to be subject to physical collapse and attrition during normal operation of the fluid reaction zone. Where an inorganic matrix is used, it is highly preferred that the matrix be substantially free of hydrocarbon conversion activity and that the matrix be substantially free of hydrogen transfer activity. If the catalyst has hydrogen transfer activity, a significant portion of the oligomers which are produced by the molecular sieve may be cracked or converted to both paraffins and aromatics which are not as chemically reactive as the olefin oligomers.

Where the molecular sieves are composited with binder materials, polymerization processes of the present invention are surprisingly more efficient with small crytallite sieve particles than with larger crystalline particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The reaction conditions under which the fluidized oligomerization reactions take place include pressures of subatmospheric to several hundred atmospheres, but preferably 10 bar or less, and most preferably 0 to 6 bar.

The reaction zone is operated below about 400° C., since above that temperature not only significant cracking of reactants and loss of oligomer product takes place, but also significant hydrogen transfer reaction causing loss of olefinic oligomers to paraffins and aromatics takes place. The reaction zone temperatures are preferably from about 150° C. and 350° C. Gas hourly space velocities sufficient to fluidize the catalyst bed are used. Gas hourly space velocities typically range from about 1000 to 3000.

Once the effluent from the oligomerization reaction zone is recovered, a number of further processing steps can be performed. The effluent of the fluidized polymerization process will contain substantial amounts of olefins of longer chain length (higher boiling point) than the feed olefins. Depending upon the molecular sieve being used and the reaction conditions, these higher boiling olefins may crack and reassemble to form a continuum of higher molecular weight compounds rather than a pure oligomeric product.

By "conversion" as used herein is meant that certain amounts of feed olefins will be converted to higher molecular weight, higher boiling olefinic products. At least 30% of the feed olefins are converted to higher boiling olefins, preferably more than 50%, and most preferably more than 70% by weight.

If it is desired to use the longer chain compounds which have been formed as mid-distillates, the olefinic product can be hydrogenated.

All or part of the effluent can be contacted with molecular sieve catalysts in further reaction zones to further react unreacted olefins and olefin oligomers with themselves and each other to form still longer chain materials. Of course, the longer the carbon chain, the more susceptible the compound is to being cracked. Therefore, where successive oligomerization zones are used, each should be operated under reaction conditions less severe than the preceding oligomerization zones. Operating with oligomerization zones in series with decreasing severity can also make process control of the exothermic oligomerization reactions much easier.

One particularly desirable and efficient method of operation is to separate unreacted olefins present in the effluent of the fluidized reaction zone from the olefin oligomers present in the effluent and then to recycle the unreacted alkenes back into the fluidized zone.

The run life of the catalyst in the oligomerization reaction zone can be greatly and surprisingly increased by periodically stopping the flow of feed into the reaction zone and stripping the catalyst with a stripping gas (such as hydrogen, nitrogen, water vapor). Alternatively, the process can be operated in a continuous rejuvenation fashion, similar to the operation of FCC units. By this is meant, two zones are used, a fluidized reaction zone in which the catalyst contacts the feed, and a stripping zone in which catalyst continuously withdrawn from the reaction zone, is contacted with stripping gas and is then continuously added back into the fluid reaction zone. A highly preferred fluidized reaction system using a single reactor with both dense and light reaction zones, is disclosed in my copending patent application Ser. No. 373,478, filed Apr. 30, 1982 and incorporated by reference.

A highly energy efficient method of operating the present process is to contact the feed with the reaction zone effluent through a heat exchanger. By this means, the heat generated by the highly exothermic oligomerization reactions can be used to heat the feed and substitute for furnace capacity.

The following examples illustrate my invention, without limiting it.

FIGURES

FIG. 1 illustrates data having differences between the hydrogen transfer indices of several catalysts as well as the response of the hydrogen transfer indices to fouling.

FIG. 2 illustrates the process scheme used in Example 3 and discussed in detail there.

EXAMPLE 1

A series of experiments was performed to examine the hydrogen transfer activity of molecular sieves. A feed pulse of fixed volume (0.5 microliter) from a heated Valco valve was carried into a small, fixed catalyst bed located in a stainless steel reactor. The reaction was entirely gas phase and isothermal. The hydrocarbon feed pulse was carried to the catalyst bed by a known velocity nitrogen stream at a high linear rate. The nitrogen stream was passed through a 4A/5A molecular sieve purifier before contacting the feed. The catalyst bed contained −250 mesh catalyst fines which, depending on the catalyst, were diluted with the same size mesh alumina. The diluent alumina was added as needed to reduce the catalyst activity so all catalysts could be measured at roughly identical feed conversions. The catalyst was finally diluted (4:1) with 80–100 mesh, acid washed Alundum to improve catalyst dispersion and to help maintain a true isothermal bed temperature. Reactor pressure was controlled by an Annin valve.

The entire gas stream, containing the reacted feed pulse, was taken directly through heated lines to the injector splitter of a capillary gas chromatograph equipped with a flame ionization detector.

The reaction conditions include a catalyst temperature of 221° C. (430° F.), total pressure of 34.5 bar (500 psi) and a nitrogen carrier gas flow of 800 cc/min. at STP. The injection volume was 0.5 microliter. Hydrocarbon analysis was performed using a 50-meter OV-101 fused silica capillary column. The catalyst was continually exposed to the nitrogen carrier gas between injections.

The hydrogen transfer index calculated from the test results is the ratio of 3-methylpentenes to 3-methylpentane produced from a 1-hexene feed, with a linear hexene conversion from 30% to 70%.

The contact time was computed from the temperatures and pressure corrected linear velocity of the nitrogen carrier stream and the length and volume of the catalyst bed. The computed WHSV and catalyst/oil ratio were based solely on the active component content within the bed.

The catalysts tested are listed in Table 1.

TABLE 1

| Catalyst | $SiO_2/Al_2O_3$ Mole Ratio |
|---|---|
| (A) ZSM-5 | 78:1 |
| (B) Silicalite | 230:1 |
| (C) Silicalite | 2200:1 |
| (D) Ultrastable Y | 6:1 |
| (E) Dealuminated Mordenite | 63:1 |
| (F) Amorphous $SiO_2/Al_2O_3$ | 54/46 (wt. ratio) |
| (G) ZSM-12 | 50:1 |

The results obtained are listed in Table 2. Experiments with Catalysts (A) and (B) were performed after impregnating the catalysts with 0.8 wt. % zinc.

TABLE 2

| Catalyst | 20% A 80% $Al_2O_3$ | 20% A 80% $Al_2O_3$ | 65% B | 65% C | 12% D 88% $Al_2O_3$ | 18% E 82% $Al_2O_3$ | 100% F | 100% G |
|---|---|---|---|---|---|---|---|---|
| Inj. Number | 3 | 3 | 3 | 2 | 3 | 1 | 2 | 1 |
| Catalyst Wt. (mg Sieve) | 4.4 | 4.1 | 19 | 24 | 2.8 | 4.2 | 35 | 19.3 |
| Zn (0.8%): Yes/No | No | Yes | Yes | No | No | No | No | No |
| Alundum Dilution | 4:1 | 4:1 | 4:1 | 3:1 | 4:1 | 4:1 | 4:1 | 4:1 |
| Contact Time (sec) | 0.25 | 0.36 | 0.33 | 0.41 | 0.28 | 0.23 | 0.34 | 0.4 |
| WHSV (1/hr) | 1100 | 806 | 200 | 120 | 1500 | 1220 | 100 | 157 |
| Cat/Oil | 13 | 12 | 57 | 71 | 9 | 13 | 104 | 57 |
| Conversion From Linear Hexenes (%) | 47 | 42 | 41 | 56 | 38 | 48 | 43 | 53 |
| $K_{Hexenes}$ (1/sec) | 2.54 | 1.51 | 1.60 | 2.00 | 1.71 | 2.84 | 1.65 | 1.88 |
| Product Yield, Wt. % | | | | | | | | |
| $C_4$ Minus | 13 | 12.6 | 14 | 13.3 | 3.5 | 17.1 | 0.3 | 12 |
| $C_5$ | 11 | 10 | 8.4 | 8.5 | 4.2 | 12.9 | 3 | 8 |
| $C_6$ | 57 | 58.8 | 62 | 53.6 | 63.2 | 55.7 | 76.4 | 73 |
| $C_7$ | 4 | 4.2 | 4.1 | 5.5 | 4.7 | 4.4 | 3.5 | 2 |
| $C_8$ | 7.5 | 5.6 | 5.4 | 7.9 | 5.9 | 5.2 | 4.1 | 3.7 |
| $C_9$ | 4 | 3.6 | 2.5 | 4.3 | 4.3 | 2.4 | 2.4 | 1.3 |
| $C_{10}^+$ | 1.9 | 2.8 | 2.3 | 4.9 | 10.7 | 1.1 | 10.1 | 0.3 |
| Hydrogen Transfer Index | | | | | | | | |
| 3M—Pentenes/ 3M—Pentane | 66 | 70 | 105 | 500 | 0.30 | 1.0 | 5 | 6 |

The graph of FIG. 1 illustrates the differences in hydrogen transfer index for several catalysts, as well as the response of the hydrogen transfer index to the number of hexene injections, i.e., to the fouling of the catalyst. The higher the hydrogen transfer index, the lower the hydrogen transfer activity of the catalyst. The hydrogen transfer index should be above 10, preferably above 25.

EXAMPLE 2

An FCC offgas fraction, the feed to a gas compressor, was collected and had the characteristics shown in Tables 3 and 4. The feed was passed over a catalyst containing zinc (1 wt. %) and silicalite (silica:alumina mole ratio 230:1; composited with alumina 65 wt.%) at a gas hourly space velocity of 1200, 10 psig (24.7 psia; 1.7 bar) and 575° F. (302° C.). The product analyses are also shown in Tables 3 and 4.

TABLE 3

| | Feed | | Product | |
|---|---|---|---|---|
| Yields | Wt. % | Mole % | Wt. % | Mole % |
| $CH_4$ | 5.0 | 14.3 | 5.0 | 15.7 |
| $C_2=$ | 4.3 | 7.1 | 3.0 | 5.6 |
| $C_2$ | 4.6 | 7.1 | 4.7 | 8.1 |
| $C_3=$ | 20.9 | 22.4 | 4.5 | 5.6 |
| $C_3$ | 5.7 | 5.9 | 6.2 | 7.1 |
| $C_4=$ | 20.3 | 16.4 | 12.4 | 11.2 |
| $iC_4$ | 11.5 | 9.0 | 13.9 | 12.2 |
| $nC_4$ | 2.6 | 2.1 | 3.6 | 3.1 |
| $C_5=$ | 8.9 | 6.1 | 11.7 | 8.6 |
| $iC_5$ | 7.5 | 4.7 | 9.5 | 6.6 |
| $nC_5$ | 3.0 | 1.9 | 1.5 | 1.1 |
| $C_6^+$ | 5.7 | 3.0 | 24.0 | 15.1 |
| $C_5^+$ | 25.1 | | 46.7 | |
| Average Molecular Weight | | 46 | | 52 |

TABLE 4

| | Feed | With Conversion Process |
|---|---|---|
| Volume, BPOD of $C_5^+$ | 2800 | 5650 |
| liquid recovered Simulated D 86, LV %, °F. (°C.) of $C_5^+$ liquid recovered | | |
| St | 88 (31) | 105 (41) |
| 10 | 89 (32) | 108 (42) |
| 30 | 92 (33) | 114 (46) |
| 50 | 97 (36) | 140 (60) |
| 70 | 105 (41) | 171 (77) |
| 90 | 138 (59) | 235 (113) |
| EP | 210 (99) | 329 (165) |
| Gravity, °API | 83.3 | 77.9 |

These data show that significant increases in liquid product and significant decreases in the gas load on a compressor can be achieved. The process doubles the amount of gasoline and reduces the compressor gas load by about 19%. These benefits are achieved at the expense of propene, reduced by 78%, and $C_4$ olefins, reduced by 39%.

EXAMPLE 3

A comparison of standard FCC light gas recovery using standard process sequences and the preferred fluidized process scheme of my invention were performed using standard computer simulation techniques.

In the comparison simulation, an FCC overhead fraction feed is passed to a condensation unit at 95° F. (35° C.) and 8 psig (22.7 psia; 1.56 bar) at a rate of about 25000 SCFM. The liquids are recovered and the remaining gas is passed at 21000 SCFM through a compressor to a second condensation unit maintained at 100° F. (37.8° C.) and 110 psig (124.7 psia; 8.6 bar). The product recovered from the second condensation unit for comparison to my process includes 14000 SCFM of light gas, and 6900 bbl per operating day of liquid, of which 2800 bbl per operating day is $C_5+$ product.

The preferred process scheme of my invention is illustrated in FIG. 2. The same FCC light gas fraction used in the comparison is fed to the same condensation unit (1) under the same conditions of 95° F. (35° C.) and 8 psig (22.7 psia; 1.56 bar). The gas, at the same rate of 21000 SCFM, is then fed through line 2 to furnace 4 for heating; a portion of line 2 passes through heat exchanger 3 where the feed stream of line 2 gains heat from the product stream of line 6. The heated feed stream is passed from furnace 4 through line 5 to the fluidized oligomerization zone (7). The oligomerization zone operation is premised on 575° F. (302° C.), 10 psig (24.7 psia; 1.7 bar) and 1200 GHSV and a zinc/silicalite catalyst; which is to say it is based on the results of Example 2 above. The oligomerized effluent is passed from the oligomerization reaction zone (6) through line 7 by way of the heat exchanger (3) through a cold water condensation unit (8). The partially condensed effluent is then passed through line 9 to an optional separation zone (10) maintained at 95° F. (35° C.) and 8 psig (22.7 psia; 1.56 bar). A liquid product of 1800 bbl per operating day, of which 1650 bbl per operating day is $C_5+$ liquid, is recovered; a gaseous product of 17000 SCFM is recovered. The gas is carried by line 11 to the compressor (12) corresponding to the compressor in the standard gas recovery process; the compressor here, however, need operate on 4000 SCFM less gas than in the comparison simulation. The compressed gas is carried by line 13 to condensation zone 14 operated at 100° F. (37.8° C.) and 110 psig (124.7 psia; 8.6 bar). Liquid is recovered at a rate of 8000 bbl per operating day, of which 4000 bbl per operating day is $C_5+$ liquid, while only 9200 SCFM gas is recovered.

As compared to the standard gas recovery system, the gas that needs to be handled is reduced by 19% while the $C_5+$ liquids (gasoline) output is increased by 2850 bbl per operating day.

My invention, and its equivalents, are claimed below.

I claim:
1. A process for oligomerizing olefins comprising:
    (a) fluidizing a fluidizable oligomerization catalyst comprising an essentially aluminum-free intermediate pore size silicaceous crystalline molecular sieve having a silica:alumina mole ratio greater than about 200:1 with a feed including gaseous olefins in an oligomerization reaction zone; and
    (b) converting at least 30% of said gaseous olefins to higher boiling olefins by maintaining oligomerization reaction zone at oligomerization conditions including a temperature of less than 400° C. and a gas hourly space velocity of said feed sufficient to fluidize at least a portion of said catalyst.
2. A process for treating a normally gaseous component of the effluent from a catalytic cracking zone, said component including normally gaseous olefins, comprising:
    (a) fluidizing a fluidizable oligomerization catalyst comprising an essentially aluminum-free intermediate pore size silicaceous crystalline molecular sieve having a silica:alumina mole ratio greater than about 200:1 with at least a portion of said normally gaseous component in an oligomerization reaction zone; and
    (b) converting at least 30% of said normally gaseous olefins to higher boiling olefins by maintaining said oligomerization reaction zone at oligomerization conditions including a temperature of less than 400° C. and a gas hourly space velocity of said normally gaseous component sufficient to fluidize at least a portion of said catalyst.
3. The process of claim 1 wherein said olefins comprise $C_3$ and $C_4$ olefins.
4. The process of claim 1 or 2 wherein said oligomerization catalyst comprises attrition-resistant essentially aluminum-free intermediate pore size silicaceous crystalline molecular sieve particles.
5. The process of claim 1 or 2 wherein said molecular sieve is silicalite or a crystalline metal organosilicate disclosed in U.S. Pat. No. Re. 29,948.
6. The process of claim 1 or 2 wherein said silica:alumina ratio is greater than about 500:1.
7. The process of claim 6 wherein said silica:alumina ratio is greater than about 1000:1.
8. The process of claim 4 wherein said catalyst further comprises zinc or a compound thereof.
9. The process of claim 5 wherein said catalyst further comprises zinc or a compound thereof.
10. The process of claim 1 or 2, further comprising:
    contacting through heat exchanging means at least part of the effluent of said oligomerization zone with said feed.
11. The process of claim 1 or 2, further comprising:
    periodically removing said catalyst from contact with said feed;
    stripping said catalyst with a stripping gas; and
    recontacting said catalyst with said feed.
12. The process of claim 11 wherein said stripping gas is steam.
13. The process of claim 1 or 2, further comprising:
    hydrogenating at least part of the effluent of said oligomerization reaction zone.
14. The process of claim 1 or 2 further comprising:
    introducing at least part of the olefin oligomers present in the effluent from said oligomerization reaction zone into at least one further oligomerization reaction zone.
15. The process of claim 14 wherein said olefin oligomers are contacted in said further oligomerization reaction zone with an intermediate pore size silicaceous molecular sieve under reaction conditions such that at least some of said oligomers are liquids.

* * * * *

UNITED STATES PATENT AND TRADEMARK OFFICE
CERTIFICATE OF CORRECTION

PATENT NO. : 4,417,087
DATED : November 22, 1983
INVENTOR(S) : Stephen J. Miller It is certified that error appears in the above-identified patent and that said Letters Patent are hereby corrected as shown below:

Col. 3, line 33, "5.0 and 6.5" should read --5.0 to 6.5--.

Col. 4, line 15, "in Re. 29,948" should read --in RE 29,948--.

Col. 4, line 23, "Re." should read --RE--.

Col. 4, line 26, "Serial No." should read --patent application Serial No.--.

Col. 5, line 2, "crytallite" should read --crystallite--.

Col. 10, line 26, "Re." should read --RE--.

Signed and Sealed this

Fourth Day of September 1984

[SEAL]

Attest:

GERALD J. MOSSINGHOFF

Attesting Officer           Commissioner of Patents and Trademarks